(12) United States Patent
Schulz

(10) Patent No.: US 10,570,070 B2
(45) Date of Patent: Feb. 25, 2020

(54) HIGH EFFICIENCY FUEL CELL

(71) Applicants: Helmut Schmidt Universität, Universität der Bundeswehr Hamburg, Hamburg (DE); Hamburg Innovation GmbH, Hamburg (DE)

(72) Inventor: Detlef Schulz, Hamburg (DE)

(73) Assignees: Helmut Schmidt Universität, Universität der Bundeswehr Hamburg, Hamburg (DE); Hamburg Innovation GmbH, Hamburg (DE)

( * ) Notice: Subject to any disclaimer, the term of this patent is extended or adjusted under 35 U.S.C. 154(b) by 0 days.

(21) Appl. No.: 15/970,080

(22) Filed: May 3, 2018

(65) Prior Publication Data

US 2018/0251409 A1    Sep. 6, 2018

Related U.S. Application Data

(63) Continuation of application No. 14/777,862, filed as application No. PCT/EP2014/055909 on Mar. 25, 2014, now Pat. No. 10,023,506.

(30) Foreign Application Priority Data

Mar. 25, 2013   (EP) .................................. 13160858

(51) Int. Cl.
*C07C 1/04* (2006.01)
*C25B 15/02* (2006.01)
(Continued)

(52) U.S. Cl.
CPC ............ *C07C 1/0485* (2013.01); *C07C 1/041* (2013.01); *C25B 1/04* (2013.01); *C25B 9/18* (2013.01);
(Continued)

(58) Field of Classification Search
CPC ....... C07C 1/0485; C07C 1/041; H01M 8/186
See application file for complete search history.

(56) References Cited

U.S. PATENT DOCUMENTS 8,257,563 B2   9/2012  Hartvigsen et al.
10,023,506 B2 * 7/2018  Schulz .................... C25B 15/02
(Continued)

FOREIGN PATENT DOCUMENTS

DE    102011088613 B3   12/2012
EP         2540388 A1    1/2013
WO   WO 2013/190581 A1   12/2013

OTHER PUBLICATIONS

Chinese Office Action for Application No. CN 2014800178483 dated Jan. 17, 2017.
(Continued)

*Primary Examiner* — Nicholas A Smith
(74) *Attorney, Agent, or Firm* — Wolf, Greenfield & Sacks, P.C.

(57) ABSTRACT

Fuel cell arrangement having an improved efficiency. The arrangement comprises one or more fuel cell units 110 and a methanation unit 200 and a control unit 300. The fuel cell unit comprises a water inlet 111, a hydrogen outlet 112 and an oxygen outlet 113. The methanation unit comprises a catalyst 222, a hydrogen inlet 213, a carbon oxide inlet 214 having a first controllable valve 215 and a methane outlet 216, wherein the hydrogen outlet of the first fuel cell unit is coupled to the hydrogen inlet of the methanation unit, and the methanation unit is adapted to convert hydrogen and carbon oxide into methane, wherein the control unit is adapted to control the first controllable valve so as to obtain an optimum converting process to convert hydrogen and carbon oxide into methane.

14 Claims, 7 Drawing Sheets

(51) Int. Cl.
   *C25B 15/08* (2006.01)
   *C25B 1/04* (2006.01)
   *H01M 8/0662* (2016.01)
   *H01M 8/18* (2006.01)
   *H01M 8/0432* (2016.01)
   *H01M 8/0438* (2016.01)
   *H01M 8/04537* (2016.01)
   *H01M 8/04746* (2016.01)
   *C25B 9/18* (2006.01)

(52) U.S. Cl.
   CPC .............. *C25B 15/02* (2013.01); *C25B 15/08* (2013.01); *H01M 8/0432* (2013.01); *H01M 8/0438* (2013.01); *H01M 8/04582* (2013.01); *H01M 8/04746* (2013.01); *H01M 8/0662* (2013.01); *H01M 8/186* (2013.01); *Y02E 60/366* (2013.01); *Y02E 60/528* (2013.01)

(56) References Cited

U.S. PATENT DOCUMENTS

| 2004/0202914 | A1 | 10/2004 | Sridhar et al. |
| 2013/0048507 | A1 | 2/2013 | Kurashina et al. |
| 2014/0370414 | A1 | 12/2014 | Schulz |
| 2016/0107952 | A1 | 4/2016 | Schulz |

OTHER PUBLICATIONS

European Office Action for Application No. EP 14717417.7, dated Oct. 24, 2016.
European Office Action for Application No. EP 14717417.1, dated Jun. 28, 2017.
European Office Action for Application No. EP 14717417.1, dated Sep. 20, 2017.
International Search Report and Written Opinion for Application No. PCT/EP2014/055909, dated Jun. 4, 2014.
International Preliminary Report on Patentability for Application No. PCT/EP2014/055909, dated Oct. 8, 2015.
Canadian Office Action for Application No. CA2859292 dated Dec. 6, 2019.

* cited by examiner

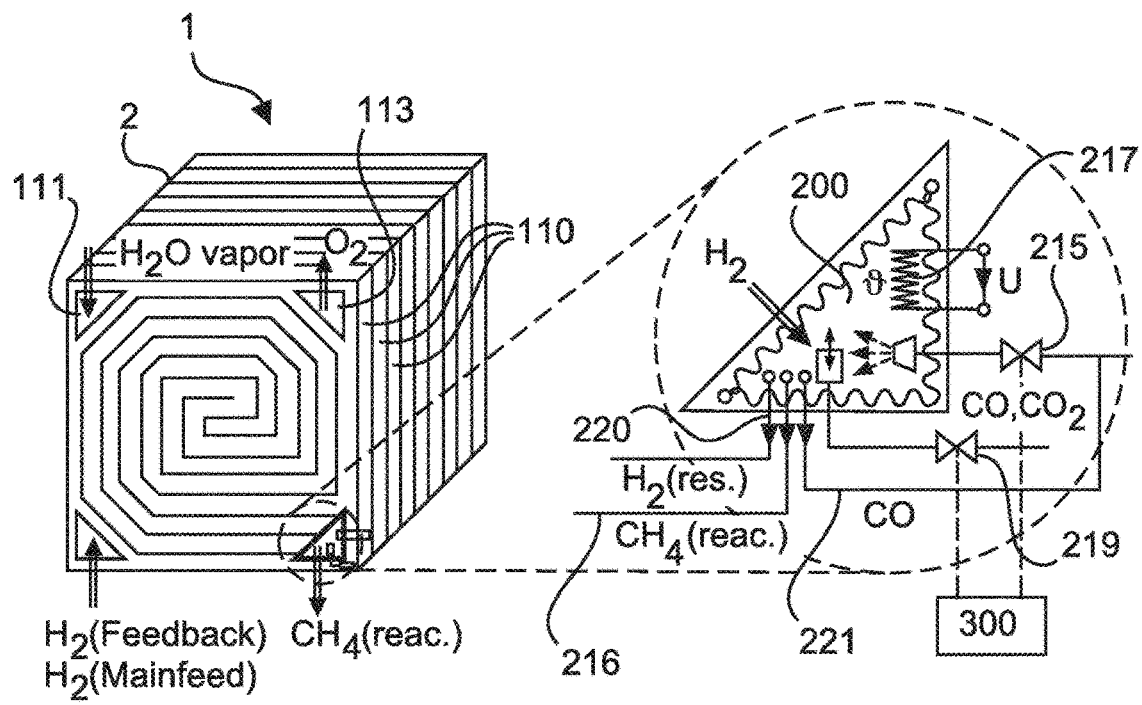
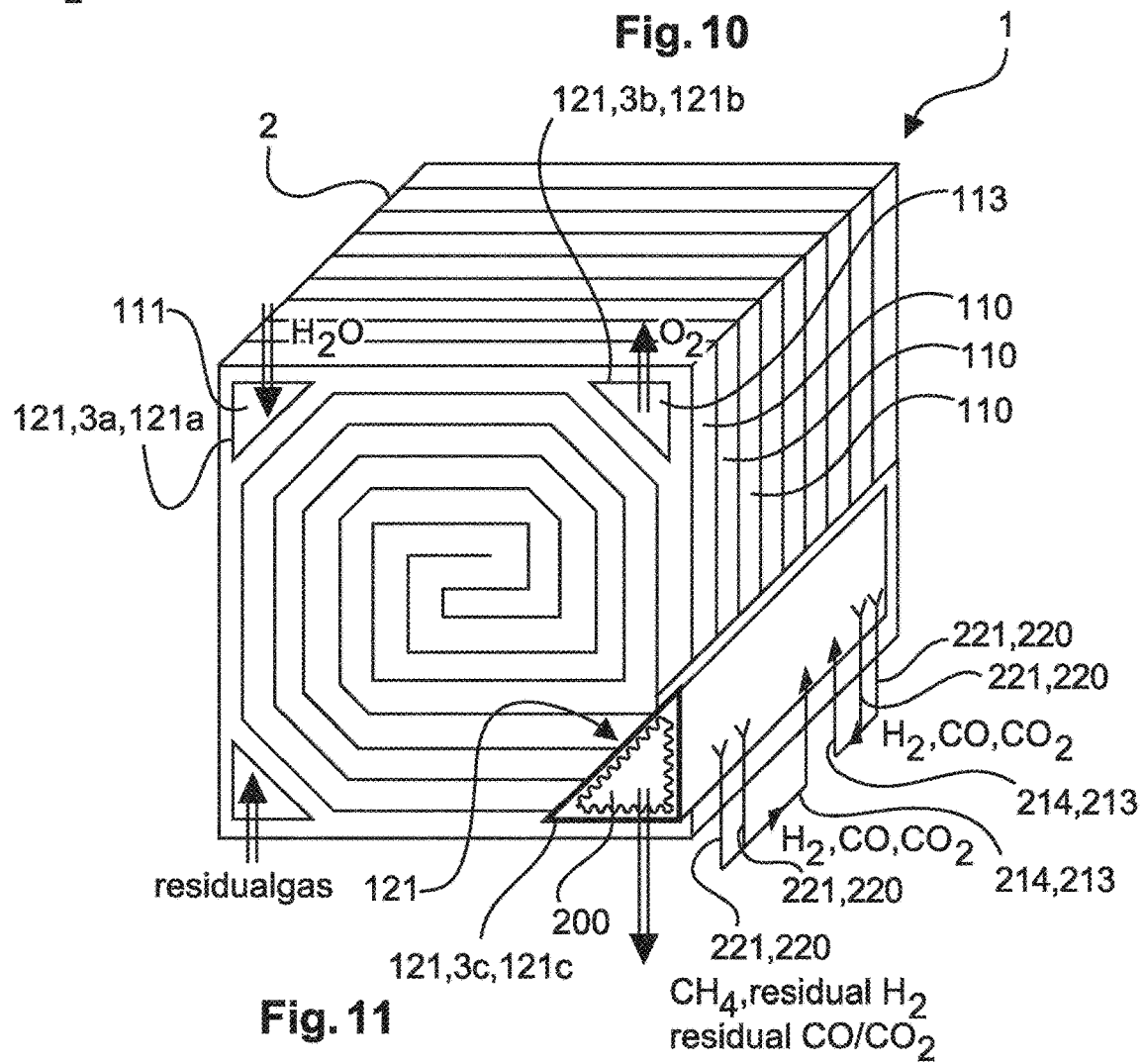
Fig. 10
Fig. 11

HIGH EFFICIENCY FUEL CELL

RELATED APPLICATIONS

This application is a continuation of U.S. patent application Ser. No. 14/777,862, filed Sep. 17, 2015, which is a national stage filing under 35 U.S.C. § 371 of International Application No. PCT/EP2014/055909, filed Mar. 25, 2014, which claims priority to European Application No. 13160858.0, filed Mar. 25, 2013. The contents of each of these applications are incorporated herein by reference in their entireties for all purposes.

FIELD OF THE INVENTION

The present invention relates to a high efficiency fuel cell, and in particular to a fuel cell including a catalyst section having a carbon oxide feedback for an methanation process.

BACKGROUND OF THE INVENTION

Fuel cells can be used for generating electricity when being fed with fuel and oxygen, for example hydrogen and oxygen. However, a fuel cell can be also operated in a reversed manner. In this case a fuel cell can be fed with electricity for conducting an electrolysis process in order to generate for example oxygen and hydrogen out of water or water vapor. When using a fuel cell in this operation mode, a fuel cell can be used to exploit an over-generation of electricity and to produce high quality fuel. This fuel can be for example stored in a much easier way than the electricity may be stored. In particular, it is easier to store hydrogen than storing an equivalent electricity or electric energy. Further, it is possible to generate a high quality fuel for other purposes, like for example heating purposes. However, handling of hydrogen may generate additional problems, as a high pressure is required for compressing hydrogen in order to reduce the storing volume. Further, using hydrogen as fuel may cause serious safety issues, as hydrogen under particular circumstances may be highly explosive. Therefore, the hydrogen may be converted into methane by way of a methanation process. In this way, hydrogen may be converted methane, so that this methane can be fed to public fuel or gas grids. Such a process is described, for example, in the Korean patent application No. 10-0814156 or Korean patent application No. 10-1093674. US 2004/0202914 describes a fuel cell arrangement having a reactor tube including a catalyst for a methanation process. The reactor tube is downstream the fuel cell and connected by conduits. A Heat exchanger by be arranged between the fuel cell and the reactor tube. DE 10 2011 088 613 describes a fuel cell having an internal actuator for controlling the fuel cell. EP 2 540 388 describes a method for operating a methanation reactor and a methanation reactor. Based on the above aspects, it may be of advantage to have a fuel cell arrangement having a higher efficiency over the prior art fuel cell arrangements.

SUMMARY OF THE INVENTION

The invention provides a high efficiency fuel cell and a method for operating the high efficiency fuel cell, a corresponding program element and computer-readable medium, according to the subject-matter of the independent claims. Further embodiments are incorporated in the dependent claims.

It should be noted that the following described exemplary embodiments of the invention apply also for the device, the high efficiency fuel cell, the method, the program element and the computer readable medium.

According to an exemplary embodiment, there is provided a fuel cell arrangement comprising a first fuel cell unit, a methanation unit, and a control unit, wherein the first fuel cell unit comprises an active part for converting water into hydrogen and oxygen, a water inlet, a hydrogen outlet, and an oxygen outlet, wherein the methanation unit comprises a catalyst, a hydrogen inlet, a carbon oxide inlet having a first controllable valve, and a methane outlet, wherein the hydrogen outlet of the first fuel cell unit is coupled to the hydrogen inlet of the methanation unit, wherein the methanation unit is adapted to convert hydrogen and carbon oxide into methane, wherein the control unit is adapted to control the first controllable valve so as to obtain an optimized converting process to convert hydrogen and carbon oxide into methane.

Thus, it is possible to control the carbon oxide feeding to the methanation unit, so as to obtain an optimized converting process. In particular, the efficiency of the fuel cell, in particular of the methanation process can be significantly increased when controlling the carbon oxide feeding to the methanation unit. It should be noted that carbon oxide may be or include carbon monoxide or carbon dioxide. Further, it should be noted that the water inlet means that the fuel cell unit may be fed with water including water in gaseous form, like water vapor. The fuel cell unit may have a cathode, an anode, and a membrane between the cathode and the anode. The hydrogen outlet of the first fuel cell unit being coupled to the hydrogen inlet of the methanation unit may be realized by a common interface between the first fuel cell unit and the methanation unit. It should be noted that the hydrogen outlet should not be exclusively understood as an embodied device, but together with the hydrogen inlet of the methanation unit may be a functional interface. In particular when providing an arrangement where the first fuel cell unit is arranged directly adjacent to the methanation unit, there may be a direct transit from the first fuel cell unit to the methanation unit serving as a hydrogen outlet and a hydrogen inlet of the fuel cell unit and the methanation unit, respectively. The control unit may control the first controllable valve based on e.g. a sensing within the fuel cell or the methanation unit. In particular, the concentration of hydrogen and/or methane and/or carbon oxide may be sensed, so as to have a base for controlling the controllable valve for feeding carbon oxide. The valve may also be controlled based on an experienced data base. The control unit may control the inlet valve so as to control the inlet of carbon oxide, e.g. carbon monoxide and/or carbon dioxide, based on a determined concentration of e.g. carbon monoxide and/or carbon dioxide and/or methane in the outlet and/or the methanation unit. Sensors can be provided for determining the above mentioned concentration. Controlling may be conducted motor driven. The controlling process may e.g. control the process so as to achieve a maximum conversation rate of carbon oxide to methane. As methanation is a catalytic process, which process requires activation energy, the optimum concentration of carbon oxide, e.g. carbon monoxide and/or carbon dioxide may vary depending on the pressure and temperature. According to an exemplary embodiment the methanation unit of the fuel cell arrangement is arranged beside the fuel cell unit in a manner to allow a heat transfer from the methanation unit to the fuel cell unit.

Thus, the heat generated in the methanation unit resulting from the exothermic methanation process may be used to heat the fuel cell unit.

According to an exemplary embodiment, the methanation unit and the fuel cell unit share a common wall. The common wall may allow a direct heat transfer from the methanation unit to the fuel cell unit. The common wall may be a separator between a fuel cell volume/cavity and a catalyst volume/cavity. The common wall may have openings for transferring hydrogen from the fuel cell cavity to the catalyst cavity. The common wall may be designed as having a porous area for transferring hydrogen. The porous area, in particular the porosity of the porous area may be controlled by an actuator, e.g. a piezo actuator. The activation of the actuator may be conducted by the control unit. The control process may be based on a look-up table being implemented in the control unit.

According to an exemplary embodiment, the fuel cell arrangement includes the fuel cell unit and the methanation unit so as to allow an internal methanation process. This can be provided by arranging the fuel cell unit beside the methanation unit, in particular when sharing a wall allowing a heat transfer between the fuel cell unit and the methanation unit. The methanation unit may conduct a primary internal methanation. In other word, it is also possible to provide an optional further subsequent methanation unit, which subsequent methanation unit may be located inside or outside a common housing including a fuel cell and the (primary) methanation unit.

According to an exemplary embodiment, the fuel cell arrangement further comprises a plurality of fuel cell units, one thereof is the first fuel cell unit, wherein each of the fuel cell units comprises a water inlet, a hydrogen outlet and an oxygen outlet, wherein the methanation unit comprises a plurality of a carbon oxide inlets, each having a controllable valve, wherein the hydrogen outlet of each of the plurality of fuel cell units is coupled to the hydrogen inlet of the methanation unit, wherein the control unit is adapted to control the plurality of controllable valves so as to obtain an optimized converting process to convert hydrogen and carbon oxide into methane.

Thus, it is possible to consider a locally varying concentration of methane in the methanation unit and to control a feeding back or even forward of carbon oxide depending on the local concentration of methane and/or hydrogen and/or carbon oxide. Thus, a proper quantity of carbon oxide may be fed back or forward to the respective one of the plurality of carbon oxide inlets of the methanation unit, so that an adapted controlling of the concentration of carbon oxide, methane, and/or hydrogen can be carried out within the methanation unit. In particular, as already described above, the plurality of hydrogen outlets of the plurality of fuel cell units may directly transit into the hydrogen inlet of the methanation unit. The hydrogen inlet of the methanation unit may extend over a range of the methanation unit corresponding to the extension of the plurality of fuel cell units adjacent to the methanation unit. It should be noted that the hydrogen inlet of the methanation unit may be an arrangement comprising a plurality of conduits between the fuel cell units and the methanation unit, but may also be a common rail hydrogen inlet receiving the plurality of hydrogen outlets of the fuel cell units.

According to an exemplary embodiment, the methanation unit comprises a plurality of methanation sub-sections, wherein each of the methanation sub-sections is allocated to one of the plurality of fuel cell units, wherein each of the methanation sub-sections comprises one of the plurality of the carbon oxide inlets, each having a controllable valve.

Thus, in certain sections of the fuel cell arrangement, a one-to-one correspondence between a fuel cell unit and a respective methanation sub-sections may be established, which may simplify the controlling of the methanation process in the entire methanation unit. However, it should be noted that it is also possible to allocate two or more fuel cell units to one methanation sub-section, or two or more methanation sub-sections to a fuel cell unit. It should be noted that it is also possible to not have a correspondence of the number of fuel cell units and the number of methanation sub-sections.

According to an exemplary embodiment, the methanation unit comprises at least one heating element.

The methanation process may be accelerated when increasing the temperature. In particular when using a fuel cell unit of a low-temperature type, the heat generation of the fuel cell unit or fuel cell units may not be sufficient for obtaining an optimized methanation process. A heating element may provide the required temperature in the methanation unit so as to optimize the methanation process. It should be noted that a plurality of heating elements may be used for providing a respective temperature profile along the extension of the methanation unit so as to control the methanation process by locally controlling the operation conditions in the methanation unit. It should be noted that, in particular when using a high temperature fuel cell unit, also cooling elements may be applied to the methanation unit, in case the temperature of the fuel cell unit should be too high for an optimized methanation process. Methanation is an exothermic reaction at high temperatures of e.g. 300° C. to 700° C. A catalyst, e.g. nickel, and adding activation energy promote the reaction. The reason for that is a slow reaction of hydrogen. In molecular form hydrogen is slow in reaction (inert). Heating converts hydrogen from molecular form into atomic form. The latter is faster in reaction. The amount of activation energy depends on the pressure. 1 bar requires 100 kJ/mol. At higher pressure, the amount of activation energy is smaller. At e.g. 4 bar the activation energy is about 75 kJ/mol According to an exemplary embodiment, the methanation unit comprises at least one sensor for sensing operation parameters in the methanation unit, wherein the sensor is selected from a group, the group consisting of a pressure sensor, a methane sensor, a hydrogen sensor, a temperature sensor, a carbon oxide sensor, wherein the control unit is adapted to control the valve based on the sensing of the sensor.

Thus, the particular operation conditions of the methanation unit may be sensed so as to provide a base for a controlling process of the carbon oxide feeding valve. It should be noted that in particular the methane sensor, the hydrogen sensor and/or the carbon oxide sensor may be sensors being capable of sensing the concentration of the respective media. It should be noted, that along the methanation unit, a plurality of sensors of each type may be provided so as to detect a local distribution of the operation conditions of methanation unit so as to provide a proper base for controlling the plurality of carbon oxide feeding valves.

According to an exemplary embodiment, the heating element is controllable upon sensed operation parameters in the methanation unit.

This allows for controlling a temperature profile along the extension of the methanation unit.

According to an exemplary embodiment, the methanation unit comprises at least one pressure controlling valve, wherein the pressure controlling valve is controllable upon sensed operation parameters in the methanation unit.

Thus, it is possible to control the methanation process not only by the measure of feeding carbon oxide to the methanation unit, but also by controlling the pressure within the methanation unit. In particular, controlling the pressure in the methanation unit may be used for fine tuning the methanation process. It should be noted that also a plurality of pressure controlling valves may be provided along the extension of the methanation unit.

According to an exemplary embodiment, the methanation unit further comprises at least one hydrogen residual gas outlet.

Thus, it is possible to take hydrogen out of the methanation unit, in particular residual hydrogen not being converted into methane. The residual hydrogen may be fed back to the methanation unit. In particular, the hydrogen may be fed back to a section of the methanation unit, where it is expected or sensed that the hydrogen rate is low.

According to an exemplary embodiment, each of the plurality of fuel cell units comprises a cathode and an anode and a fuel cell membrane between the cathode and the anode, wherein at least one fuel cell membrane comprises a controllable electrode arrangement, and the fuel cell arrangement further comprises an electrode arrangement controlling unit.

Thus, it is possible to control the fuel cell electrolysis process and to quickly react on an overheating condition. In particular, it is possible to directly control the membrane, and to carry out the controlling at the very core element of the fuel cell unit. This allows a quick response and fast feedback of the controlling procedure of the fuel cell units.

It should be noted that the electrode arrangement may be a multiple electrode arrangement, for example a grid or a pattern having a horizontal grid crossed by a vertical grid. It should be noted that the horizontal grid and the vertical grid may be arranged distantly so as to be isolated. The electrode arrangement may be arranged on the surface of the membrane or in the volume of the membrane. It is also possible to provide one part of the electrode arrangement on the one surface side of the membrane, and a further part of the electrode arrangement on the other surface side of the membrane. It should be noted, that also alternative controlling parameters may be used for controlling the fuel cell operation process, i.e. the electrolysis. In particular alternative impacts to an electrical impact may be provided, like for example a light impact, a pressure impact, a temperature impact, or any other impact being proper for controlling the fuel cell process.

According to an exemplary embodiment, the fuel cell arrangement comprises at least one di/dt measuring unit, wherein the electrode arrangement controlling unit is adapted to control the electrode arrangement based on the measured or sensed di/dt.

Thus, it is possible to measure the current gradient and to conclude from the measured or detected or sensed current gradient the condition of the fuel cell, so that the fuel cell may be controlled properly by controlling the electrode arrangement. In particular when detecting a high current gradient, like a fast increasing of the current, it is necessary to quickly react with a controlling process so as to avoid damages of the fuel cell arrangement.

According to an exemplary embodiment, the methanation unit comprises an active wall surface section being coated with a catalyst agent.

Thus, it is possible to provide an easy construction of a catalyst. It should be noted, that the active wall surface section may be pleated or may be formed in a surface-increasing manner so that the active surface of the catalyst agent is high. Thus, the methanation process may be improved and increased with respect to efficiency.

According to an exemplary embodiment, the catalyst agent is a solid phase catalyst material selected from a group, the group consisting of nickel, aluminum oxide, zirconium oxide, noble metals, in particular platinum and platinum alloys.

In particular solid phase catalysts are easy to handle and the geometry on a regular basis maintains constant. In particular, a dosing issue of the catalyst agent may be avoided.

According to an exemplary embodiment, the plurality of fuel cell units are stacked.

Thus, it is possible to provide a compact design of the fuel cell arrangement, for example having a plurality of stacked fuel cell units and a methanation unit extending along the stack of the fuel cell units.

According to an exemplary embodiment, the fuel cell arrangement further comprises a rectangular housing, wherein each fuel cell unit has a rectangular envelope with at least one cut-off edge, wherein the cut-off edges of each of the plurality of fuel cell units correspond to each other, so as to form a channel for ducting gas.

Thus, it is possible to provide an optimized geometry. The cut-off edge may result in a channel having e.g. a triangular cross-section, so that the channel can be placed adjacent to the corresponding cut-off edges, but within the rectangular housing of the fuel cell arrangement.

According to an exemplary embodiment, the fuel cell arrangement further comprises a rectangular housing, wherein each fuel cell unit has a rectangular envelope with three cut-off edges, wherein the three cut-off edges of each fuel cell unit correspond to each other so as to form at least three channels for ducting gas, a first channel serving for providing water vapor, a second channel serving for oxygen collection, and a third channel serving for receiving the methanation unit, wherein the hydrogen outlet of each of the plurality of fuel cell units is coupled to at least one of the hydrogen inlets of the methanation unit.

Thus, within the rectangular housing of the fuel cell arrangement, the cut-off edges of the fuel cell units provide space for providing channels for ducting a gas. In particular, it is also possible to provide four channels at each of the longitudinal edges of the rectangular housing, one channel for water vapor, one channel for oxygen, one channel for the methanation unit, and one channel for a residual gas duct.

According to an exemplary embodiment, there is provided a method for improving the efficiency of a fuel cell arrangement having a first fuel cell unit and a methanation unit, wherein the first fuel cell unit comprises a water inlet, a hydrogen outlet, and an oxygen outlet, and wherein the methanation unit comprises a hydrogen inlet, a carbon oxide inlet, a first controllable valve and a methane outlet, wherein the hydrogen outlet of the first fuel cell unit is coupled to the hydrogen inlet of the methanation unit, wherein the methanation unit is adapted to convert hydrogen and carbon oxide into methane, the method comprising the step of controlling the first controllable valve for controlling a feeding of carbon oxide to the methanation unit so as to obtain an optimum converting process to convert hydrogen and carbon oxide into methane.

In particular, it should be noted that also a plurality of controllable valves may be provided along the methanation unit, so that a local distribution of the concentration of carbon oxide can be controlled, so as to have an optimization at each location of the methanation unit.

According to an exemplary embodiment, there is provided a program element, which, when being executed by a processor, is adapted to carry out the above described method.

According to an exemplary embodiment, there is provided a computer readable medium having stored the above described program element.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

FIG. 10 illustrates the general build-up of a fuel cell arrangement having stacked fuel cell units, and the interrelation of inputs and outputs of the methanation unit with respective to the fuel cell unit stack according to an exemplary embodiment of the invention.

FIG. 11 illustrates a schematic overview of a fuel cell arrangement according to an exemplary embodiment of the invention, having implemented a methanation unit and feedback lines for hydrogen and carbon oxide.

DETAILED DESCRIPTION OF EXEMPLARY EMBODIMENTS

Figure 1:
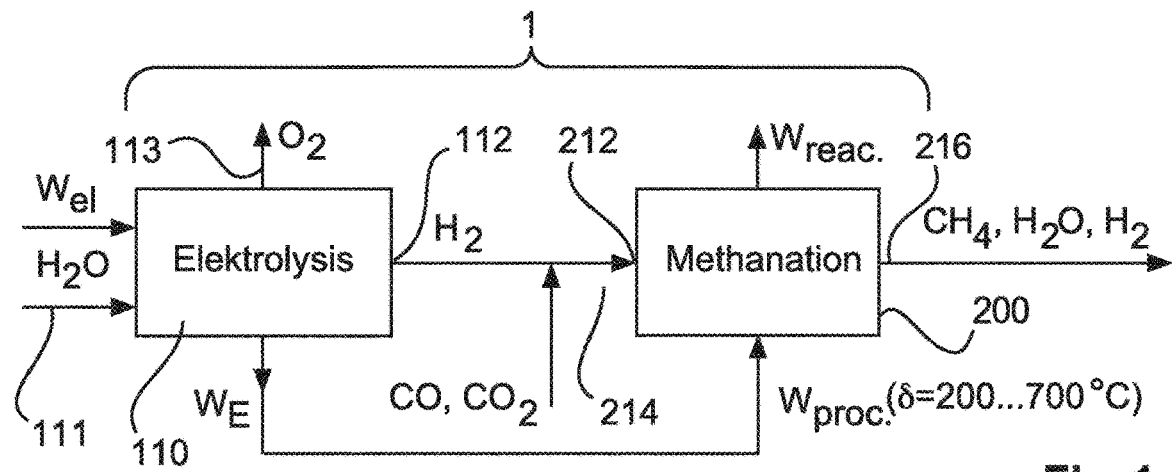
FIG. 1 illustrates a schematic overview on the process of converting electrical energy into methane according to an exemplary embodiment of the invention.

FIG. 1 illustrates a schematic overview on the process of the conversion of electric energy into oxygen and hydrogen from water by way of electrolysis, as well as the following methanation process by use of the hydrogen output of the electrolysis. As a result of the methanation, methane, $CH_4$, is produced, which may be used for methane storing purposes. Water is supplied to the fuel cell 110 by way of the fuel cell water inlet or water vapor inlet 111. The water is split up into oxygen and hydrogen by way of electrolysis and by inputting electric energy. Oxygen is supplied to the fuel cell oxygen output or outlet 113, and hydrogen is output through fuel cell hydrogen outlet 112. The fuel cell converts electric energy into heating energy $W_E$, which heating energy is used as a process energy for the methanation process. The hydrogen when leaving the electrolysis/fuel cell unit 110 through hydrogen outlet 112, enters the methanation unit 200 through methanation unit hydrogen inlet 212. The required carbon for the methanation is provided through the carbon oxide inlet 214, so that the hydrogen and carbon oxide are converted into methane supported by a catalyst. The scheme of FIG. 1 illustrates, that not only methane leaves the fuel cell arrangement, but also water, normally as vapor, and hydrogen. The general principle is to use the heat energy of the fuel cell unit to provide the heating energy for the methanation process, and to control the methanation process by controlling the input of carbon oxide. It should be noted that carbon oxide may be carbon monoxide as well as carbon dioxide. The temperature of the fuel cell arrangement, in particular the fuel cell unit may be in the range of some 100° C. up to about 1000° C. and more.

Figure 2:
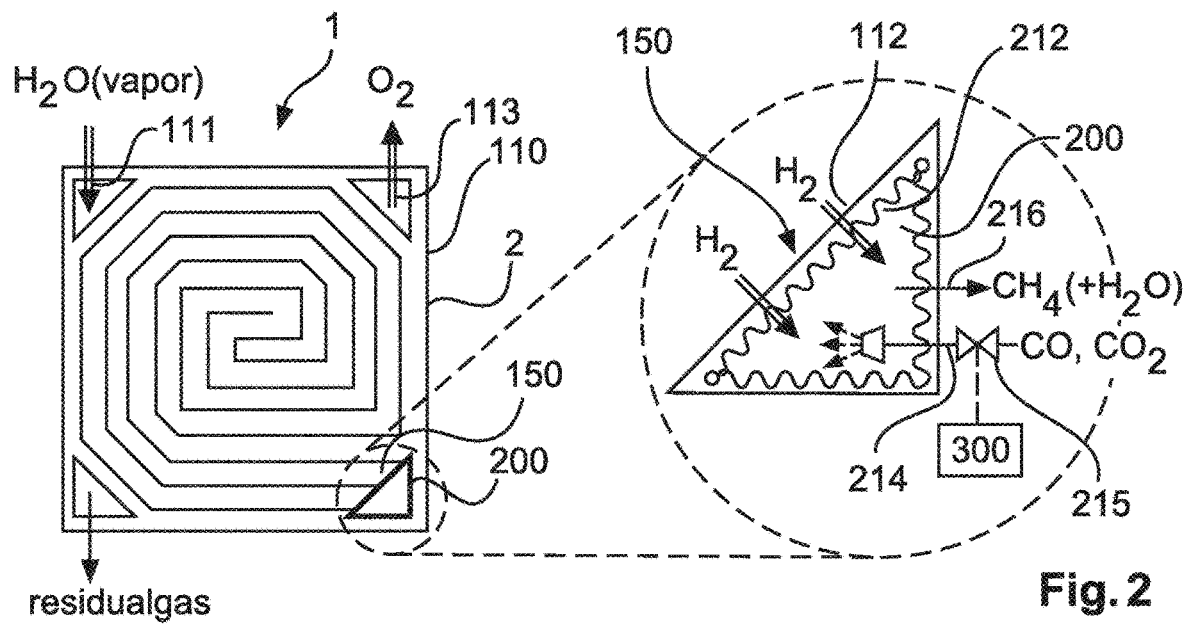
FIG. 2 illustrates a schematic overview on a fuel cell arrangement according to an exemplary embodiment of the invention, having a controlled carbon oxide feeding.

FIG. 2 illustrates the build-up of a fuel cell arrangement 1 having a fuel cell unit 110, and a methanation unit 200. The fuel cell arrangement 1 may have channels or ducts which are used for ducting gases, like water vapor, oxygen, hydrogen, etc. The left hand side of FIG. 2 illustrates a cross-sectional view of the fuel cell arrangement 1 with methanation unit 200 and a fuel cell unit 110, having a fuel cell water vapor inlet 111 and an oxygen output 113. The fuel cell unit 110 as well as the methanation unit 200 as well as the ducts or channels are provided in a fuel cell housing 2. On the right hand side, the methanation unit 200 is illustrated in an enlarged view. Hydrogen leaves the fuel cell unit 110 through the fuel cell hydrogen outlet 112, and enters the methanation unit 200 through the hydrogen inlet 212. It should be noted that the hydrogen outlet 112 and the hydrogen inlet 212 do not mandatorily require the embodied structure of a duct, but may also be considered as a direct transit from the fuel cell unit 110 and the methanation unit 200. Hydrogen enters the methanation unit 200, and the methanation unit 200 is heated by the thermal energy of the fuel cell unit, resulting from the input of electric energy and the electrolysis process. In addition, the methanation unit 200 is fed by carbon oxide through the carbon oxide inlet 214, whereas the carbon oxide amount can be controlled by the carbon oxide inlet valve 215. The controlling of the carbon oxide valve 215 may be carried out by the controlling unit 300 being coupled to the valve 215. The heat within the methanation unit as well as the catalyst agent which may be provided on wall surface sections of the methanation unit, converts the carbon oxide and the hydrogen to methane, whereas the remaining oxygen of the carbon oxide together with residual hydrogen converts into water, possibly in form of vapor. The methane exits the methanation unit through the methane outlet 216. FIG. 2 illustrates an embodiment, where the heat of the fuel cell unit is sufficient for operating the methanation process in the methanation unit 200, so that no further heat is required.

The methanation unit 200 of the fuel cell arrangement is arranged beside the fuel cell unit 110 in a manner to allow a heat transfer from the methanation unit to the fuel cell unit. The heat generated in the methanation unit 200 resulting from the exothermic methanation process may be used to heat the fuel cell unit 110. The methanation unit 200 and the fuel cell unit 110 share a common wall 150. The common wall 150 may allow a direct heat transfer from the methanation unit to the fuel cell unit. The common wall 150 may be a separator between a fuel cell volume/cavity 110 and a catalyst volume/cavity 200. The common wall 150 may have openings for transferring hydrogen from the fuel cell cavity to the catalyst cavity. The common wall may be designed as having a porous area for transferring hydrogen. The porous area, in particular the porosity of the porous area may be controlled by an actuator, e.g. a piezo actuator. The activation of the actuator may be conducted by the control unit. The control process may be based on a look-up table being implemented in the control unit. The common wall 150 may have a porous section being permanently porous allowing a basic amount of hydrogen to transit, and at the same time may have a valve controlled conduit for controlling an additional amount of hydrogen. This, the minimum amount of hydrogen may permanently transit and the additional amount may be controlled by the control unit via a valve. The fuel cell arrangement may include the fuel cell unit and the methanation unit so as to allow an internal methanation process within the fuel cell arrangement. This can be provided by arranging the fuel cell unit beside the methanation unit, in particular when sharing a wall allowing a heat transfer between the fuel cell unit and the methanation unit. The methanation unit may conduct a primary internal methanation. In other word, it is also possible to provide an optional further subsequent methanation unit, which subsequent methanation unit may be located inside or outside a common housing including a fuel cell and the (primary) methanation unit.

Figure 3:
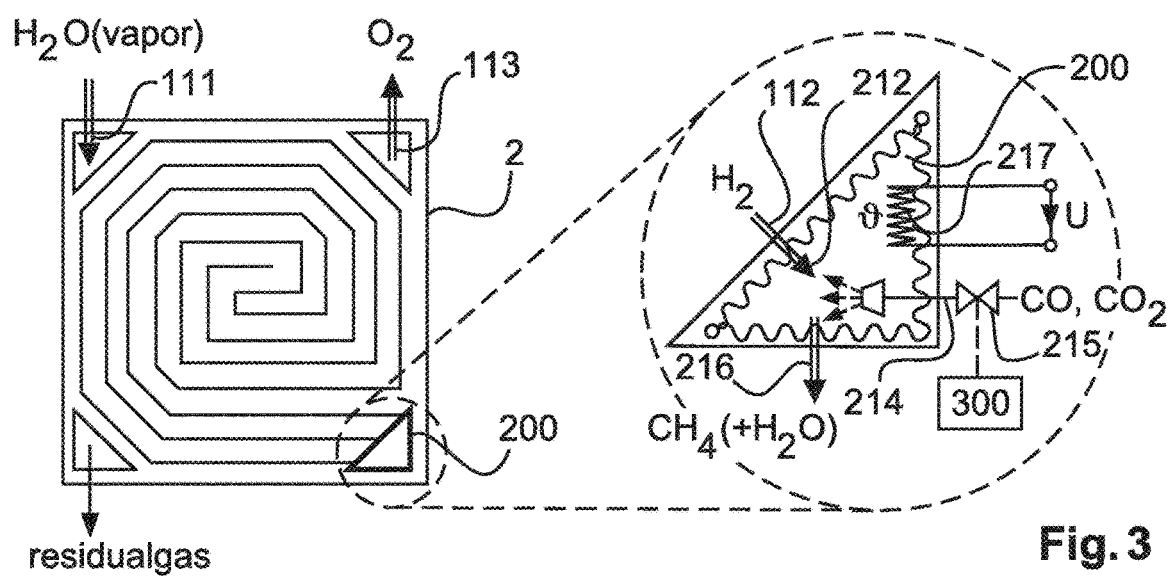
FIG. 3 illustrates a fuel cell arrangement according to an exemplary embodiment of the invention, additionally having a methane outlet in the methanation unit.

FIG. 3 illustrates a similar arrangement to that of FIG. 2. Corresponding elements are denoted with corresponding references numerals, and will not be described in further detail again. The difference between FIG. 3 and FIG. 2 is the provision of a heating element 217, which may be provided within the methanation unit 200. Additional heat provided by the heating element 217 may be required if the fuel cell unit is a low temperature fuel cell unit, and the thermal energy is not sufficient for operating the methanation process in the methanation unit 200. For this purpose, an additional heating element 217 is provided within the methanation unit. In the same way, hydrogen entering the hydrogen inlet 212 together with the fed carbon oxide will be converted into methane, which may leave the methanation unit through methane outlet 216. The carbon oxide may be fed through the carbon oxide inlet 214 and controlled by the valve 215 and the controlling unit 300. It should be understood, that the carbon oxide may be distributed within the methanation unit by way of a nozzle arrangement, which is not illustrated and described in further detail. A methanation unit 200 may have an active catalyst wall surface section 222, which may be coated with a catalyst agent, as will be described with respect to FIG. 4. It should be noted that even if not explicitly described with respect to the remaining figures, also the methanation unit 200 of FIGS. 2, 3, etc. may be provided with a methanation unit active wall surface section, which may be coated with a catalyst agent.

Figure 4:
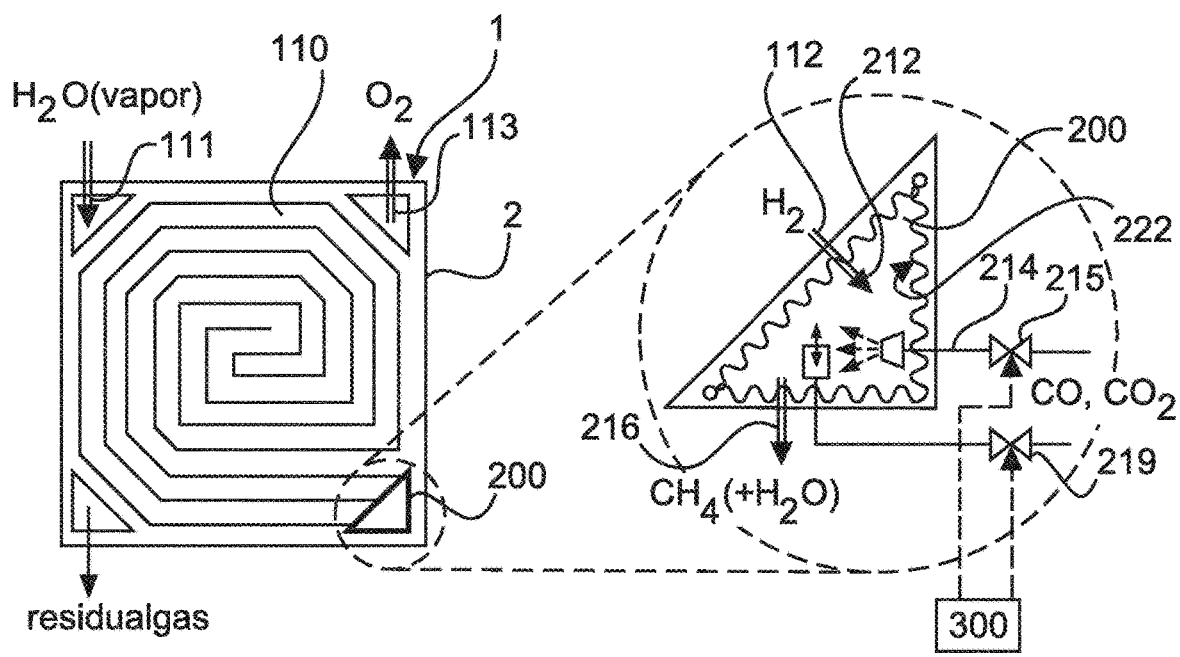
FIG. 4 illustrates a fuel cell arrangement according to an exemplary embodiment of the invention, having an additional pressure controlling valve in the methanation unit.

FIG. 4 illustrates a further exemplary embodiment which is similar to that of FIGS. 2 and 3. In addition to the structure of FIG. 2, FIG. 4 illustrates the provision of a pressure controlling valve 219 to control the pressure within the methanation unit 200. The pressure control valve may also be controlled by the controlling unit 300 so that the controlling unit 300 may control the carbon oxide feeding valve 215 as well as the pressure controlling valve 219. Similar to the structure of FIGS. 2 and 3, the hydrogen entering the hydrogen inlet 212 and the carbon oxide provided through the carbon oxide inlet 214 will be converted into methane which may leave the methanation unit 200 through methane outlet 216. It should be noted that also water vapor may leave the methanation unit through methane outlet 216. Nevertheless, water vapor may also exit the methanation unit 200 through a separate outlet, which is not illustrated and described in further detail. FIG. 4 relates to a high temperature fuel cell unit, so that a heating element may be avoided. However, it should be understood that if the heat is not sufficient, also for a high temperature fuel cell unit, one or more additional heating elements may be provided. The methanation unit 200 comprises an active wall surface section 222, which active wall surface section may be coated with catalyst agent. The active wall surface may be an inner surface of a cavity, which cavity forms the methanation unit. The active wall surface section may be corrugated so that the effective surface of the active wall surface section is enlarged. In particular when using the wall surface section as a carrier or substrate for a catalyst agent, an enlarged surface may increase the efficiency of the catalyst process. Typical catalyst agents may be solid phase catalysts, like nickel, zirconium oxide, aluminum oxide, or noble metals, and noble metal alloys, like platinum, gold, etc.

Figure 5:
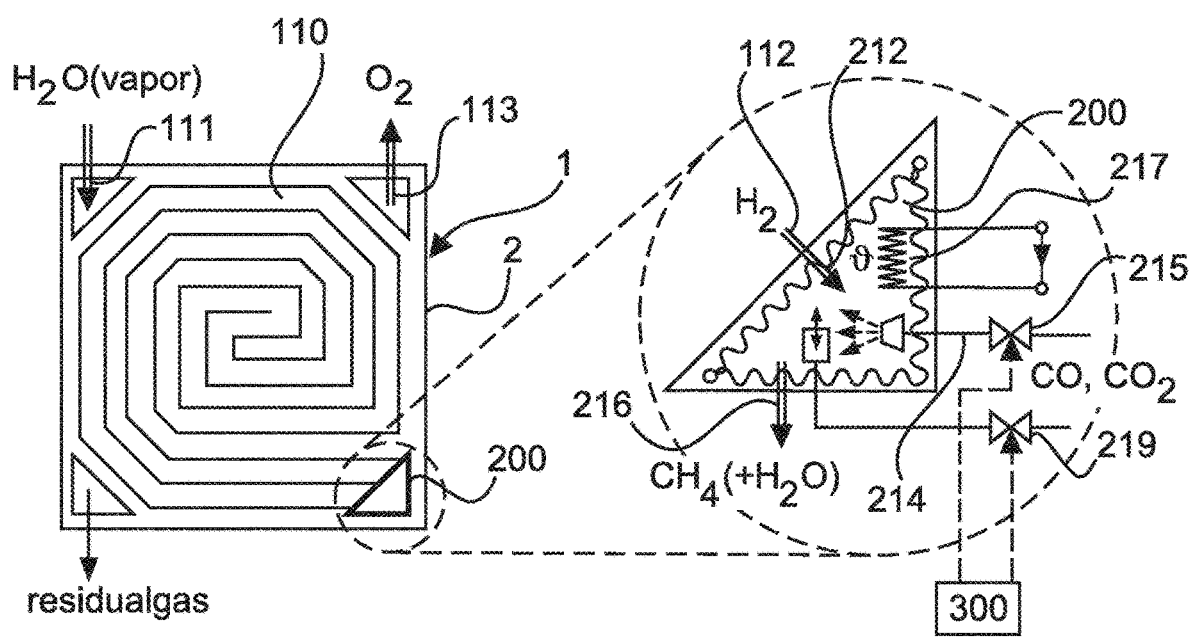
FIG. 5 illustrates a fuel cell arrangement according to an exemplary embodiment of the invention having an additional heating element in the methanation unit.

FIG. 5 illustrates a similar structure like the FIGS. 2 to 4 above. Same elements are denoted with same reference numerals and will not be described in further detail again. FIG. 5 comprises in addition to FIG. 4 a heating element 217 for heating up the methanation unit 200. Typically, the structure of FIG. 5 comprises a fuel cell unit of a low temperature type, so that additional heat required for the methanation process will be provided by the heating element 217. However, it should be noted that if the temperature is sufficiently high, even if using a low temperature fuel cell unit, the heating element 217 may be left out. In correspondence to FIG. 4, the methanation unit is provided with a pressure controlling valve 219, which pressure controlling valve may be controlled by the controlling unit 300, as well as the carbon oxide feeding valve 215.

It should be noted that the valves, sensors, pumps, control lines heaters etc. can be provided a plural times within the methanation units illustrated in FIGS. 2 to 5 and FIG. 13. In other words, each of the illustrated set of valves, sensors, pumps, control lines heaters etc. can be provided for each of the fuel cell units 110 being arranged adjacent to the methanation unit 200. The control unit 300 may each of the valves or respective groups of valves separately, so as to consider the different conditions in each of the plurality of fuel cell units 110. Thus, each of the fuel cell units can be controlled so as to achieve an optimum concentration of carbon oxide and a maximum gain of methane in the methanation unit.

Figure 6:
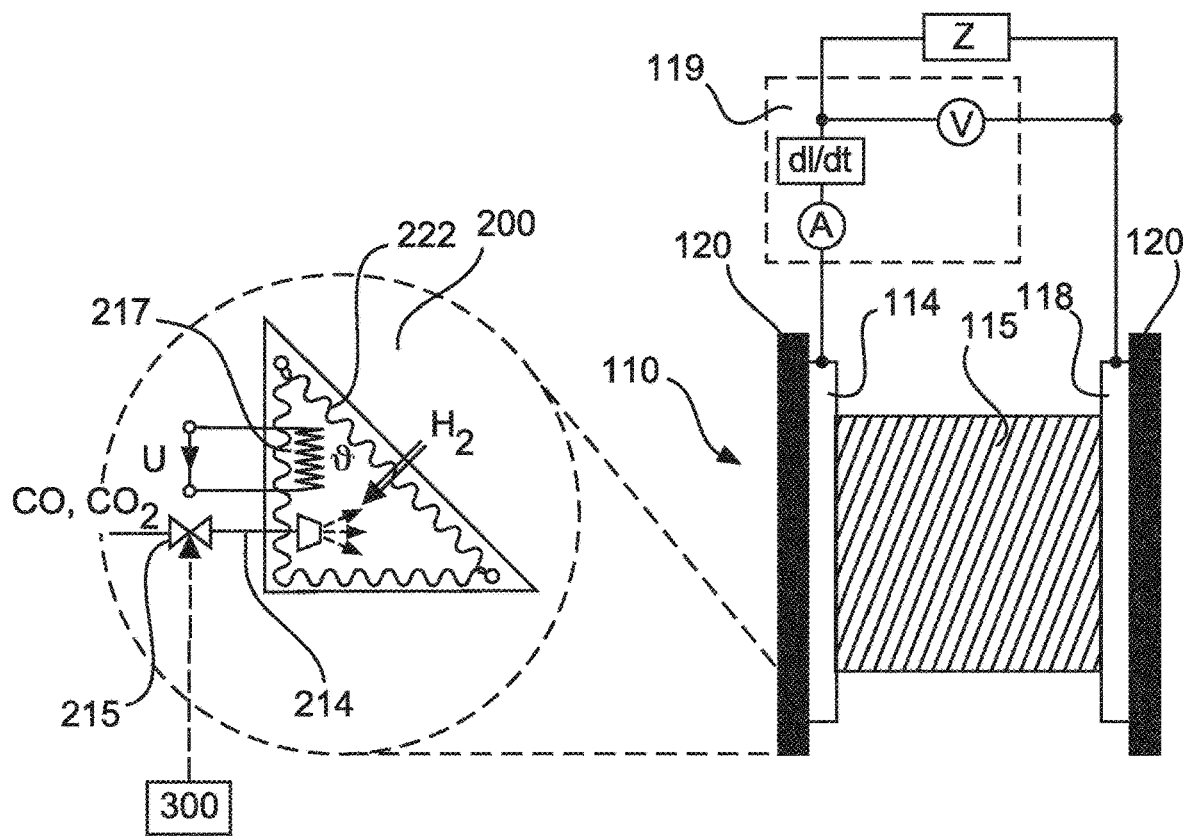
FIG. 6 illustrates a schematic overview on a fuel cell arrangement according to an exemplary embodiment of the invention, with a structure of a fuel cell unit and a heating element, and a carbon oxide control valve in the methanation unit.

FIG. 6 illustrates a schematic overview of a fuel cell arrangement, wherein the fuel cell unit is illustrated in more detail with respect to the general build-up thereof. The methanation unit 200 of FIG. 6 is similar to that of FIG. 3. The fuel cell unit comprises a fuel cell cathode 114, a fuel cell membrane 115 and a fuel cell anode 118. Additionally, gas distribution plates may be provided, which are denoted with 120. The gas distribution plates serve for a more or less equal distribution of the fed gas, in particular water vapor, oxygen or hydrogen. As can be seen in FIG. 6, the fuel cell arrangement may be further provided with a current gradient measuring unit 119, which may detect di/dt so as to detect the operating condition of the fuel cell unit. A denotes a current sensor, and V illustrates a voltage sensor. Z illustrates a load.

Figure 7:
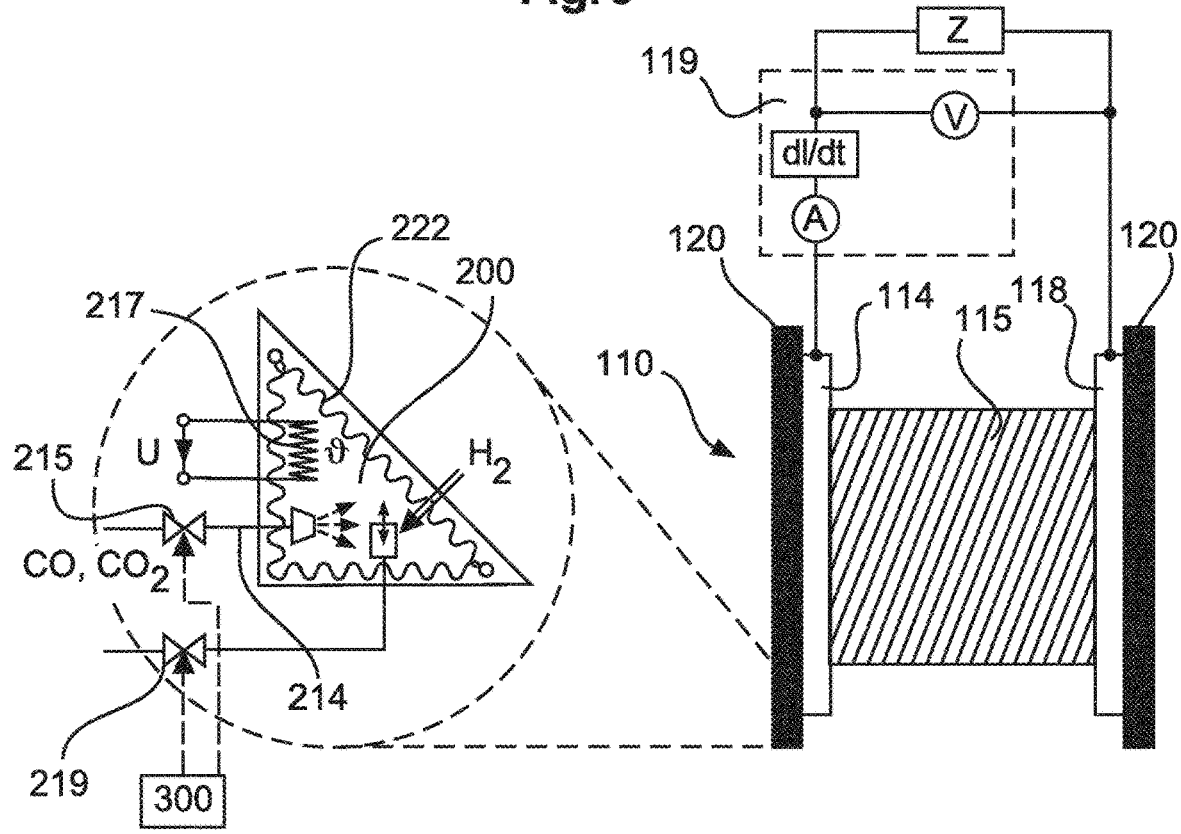
FIG. 7 illustrates a schematic overview on a fuel cell arrangement according to an exemplary embodiment of the invention, illustrating a structure of a fuel cell unit and an additional pressure controlling valve in the methanation unit.

FIG. 7 illustrates a similar structure as illustrated in FIG. 6, however with an additional pressure controlling valve 219. The pressure controlling valve 219 as well as the carbon oxide controlling valve 215 are controlled by the controlling unit 300. The build-up of the fuel cell unit 110 is similar to that of FIG. 6, and therefore will not be described in further detail again.

Figure 8:
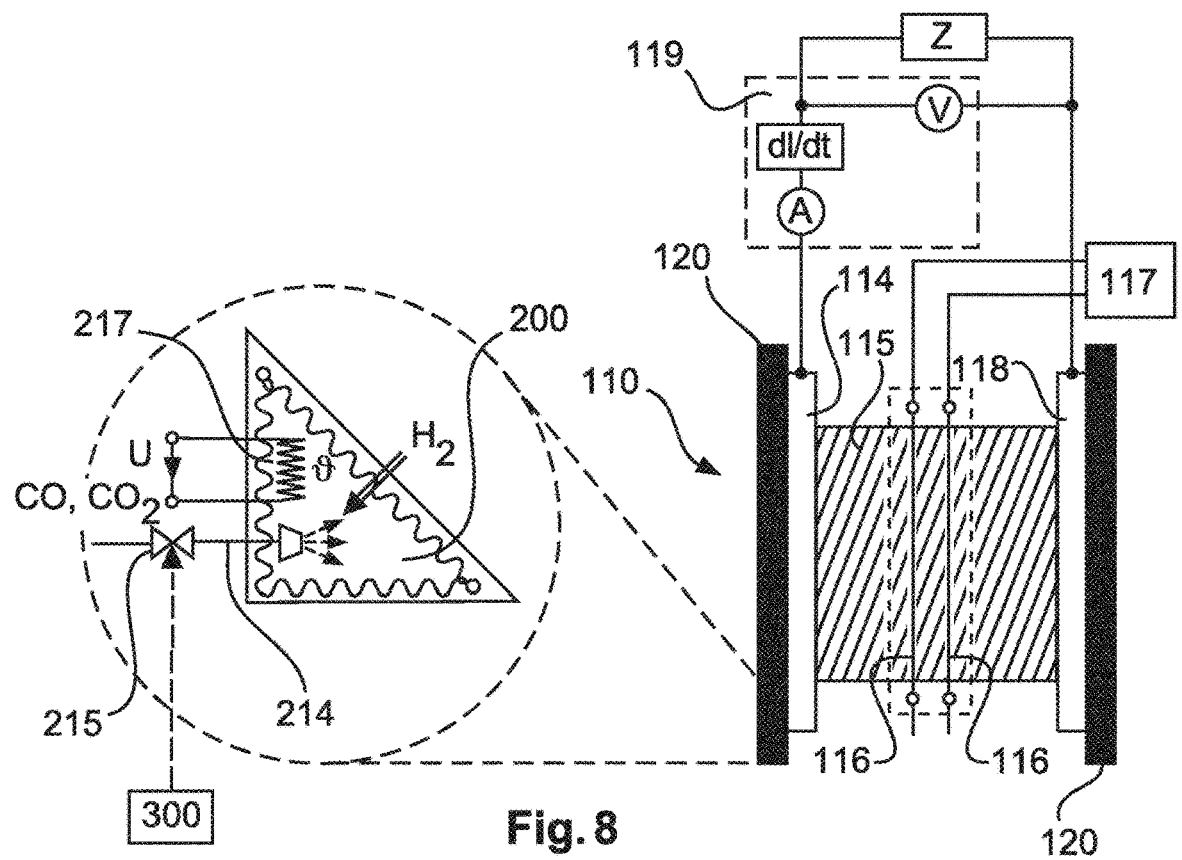
FIG. 8 illustrates a schematic overview on a fuel cell arrangement according to an exemplary embodiment of the invention, illustrating a structure of a fuel cell unit having a controlling electrode arrangement in the membrane, a heating element and a carbon oxide control valve in the methanation unit.
Figure 9:
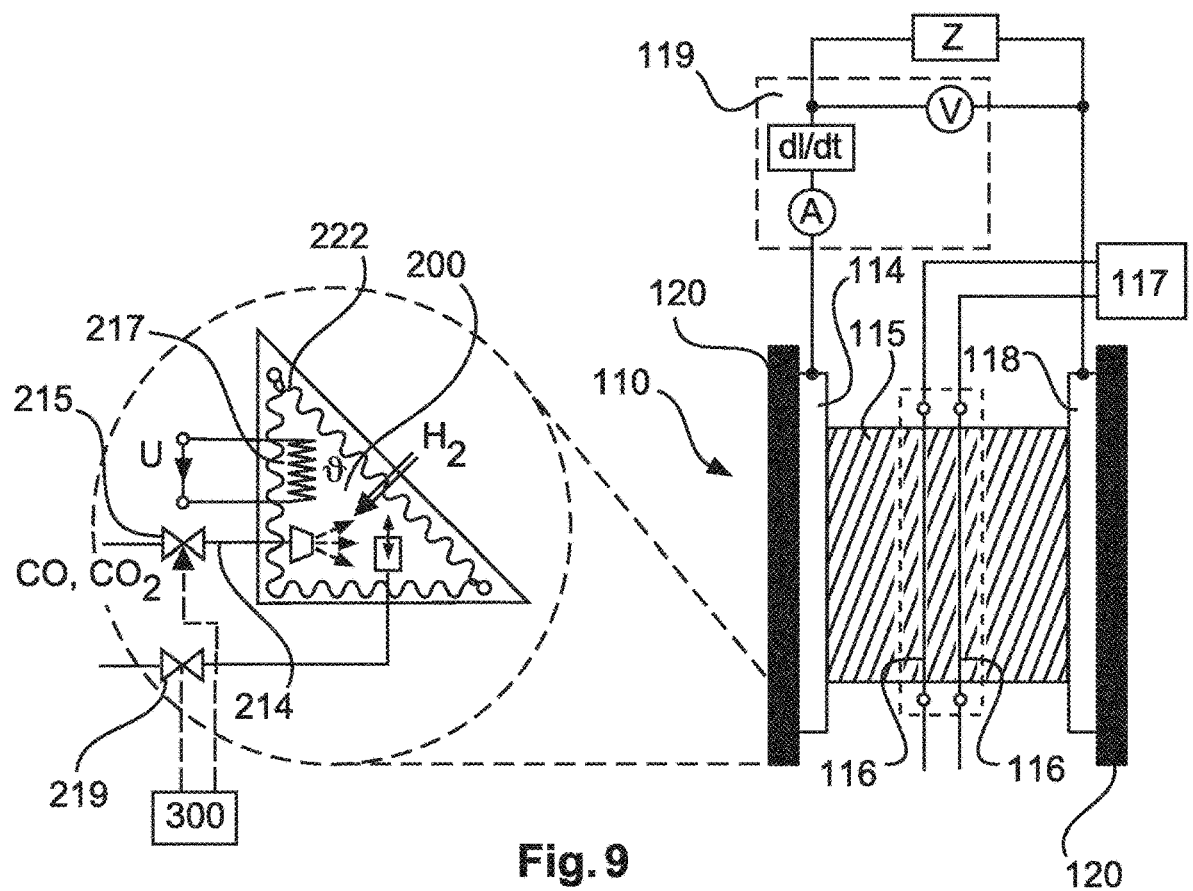
FIG. 9 illustrates a schematic overview on a fuel cell arrangement according to an exemplary embodiment of the invention, illustrating a structure of a fuel cell unit having an electrode arrangement and an additional pressure control valve in the methanation unit.

FIG. 8 and FIG. 9 correspond to the structure of FIG. 6 and FIG. 7. The methanation unit of FIG. 8 is the same as the methanation unit of FIG. 6, and the methanation unit of FIG. 9 is the same as the methanation unit of FIG. 7. Therefore, the respective methanation units will not be described in further detail again, with respect to FIG. 8 and FIG. 9. FIG. 8 and FIG. 9 illustrate a further modification of the fuel cell unit 110, which fuel cell unit may have a fuel cell membrane controlling electrode 116. The fuel cell controlling electrode 116 may be controlled by the fuel cell membrane controlling electrode controlling unit 117. The electrodes 116 may serve for a quick and fast controlling of the fuel cell unit, as the electrodes 116 act directly in or on the core element of the fuel cell, namely the membrane. Even if the electrodes 116 are illustrated as being inside the membrane, it should be understood, that the electrodes may also be provided beside the surface of the membrane, or on the surface of the membrane. The electrodes 116 may be for example a grid electrode, or for example separated horizontal and vertical electrodes, which may be controlled separately by the controlling unit 117. Even the single vertical wires or conductor stripes of the vertical or the horizontal grid may be separately controlled so as to locally control the membrane. The controlling unit 117 may control the electrode arrangement 116, based on a detected current gradient or a detected temperature, which sensing information may come from the gradient sensor 119 or e temperature sensor, respectively. It should be noted that the controlling unit 117 may be in a functional connection with the controlling unit 300, so as to dependently control the operation of the fuel cell unit as well as the controlling of the methanation unit.

FIG. 10 illustrates a further exemplary embodiment of a fuel cell arrangement 1 within a housing 2 with the water vapor inlet 111, and the oxygen outlet 113. The fuel cell arrangement 1 may comprise a plurality of fuel cell units 110, which may be arranged in a stacked manner. The methanation unit 200 may be provided in a corner of the housing 2, which free space may result from corresponding cut-off edges of the fuel cell units 110. The methanation unit 200 is illustrated in an enlarged view on the right hand side, illustrating a plurality of further elements, like for example the heating element 217, which was described with respect to FIGS. 3 and 5 in more detail. A methanation unit 200 may further comprise the carbon oxide feeding inlet, being controlled by a carbon oxide controlling valve 215. In addition, the pressure can be controlled within the methanation unit by way of a pressure controlling valve 219. The pressure controlling valve 219 and the carbon oxide controlling valve 215 may be controlled by the controlling unit 300. The methanation unit further may have a carbon oxide outlet, for which outlet residual carbon oxide may leave the methanation unit 200. The residual carbon oxide may be fed back or forward to the carbon oxide inlet so as to re-enter the methanation unit. It should be noted that the re-entering may take place at a different location depending on the concentration of carbon oxide within the methanation unit. The methanation unit further may have a methane outlet 216 as well as an additional outlet 220 for residual hydrogen. Residual hydrogen may also be fed back or forward to the methanation unit, for example to a location having a lower hydrogen concentration within the methanation unit. The feedback process will be described in further detail with respect to FIG. 11.

FIG. 11 illustrates the principle of gas feedback. The general build-up of the fuel cell arrangement 1 is similar to that described above. The methanation unit 200 may have for example a plurality of hydrogen outlets 220 or carbon oxide outlets 221. Although illustrated as the same duct, it should be understood that the outlets for hydrogen and the outlets for carbon oxide may be different ones, so that the amount of gas may be controlled separately. FIG. 11, however, does not illustrate in further detail the possibility of separately controlling hydrogen and carbon oxide. The hydrogen concentration at the center of the methanation unit 200 is lower as well as the concentration of carbon oxide, and the concentration increases to the end sections. So that typically the outlets for residual hydrogen and carbon oxide are at the end sections of the methanation unit 200, and the inlets are in the middle thereof. It should be noted that a plurality of residual hydrogen outlets and carbon oxide outlets may be controlled differently, so that a concentration may be controlled very exactly over the length of the methanation unit. Thus, the entire process of methanation may be created very efficiently.

FIG. 11 also illustrates the position of the channels, which are formed by the cut-off edges of the rectangular enveloped fuel cell units 110. The corresponding cut-off edges form a channel 3, 3a, 3b, 3c for receiving a gas duct. The corresponding cut-off edges 121a of the fuel cell units form the channel 3a for ducting a gas, here the fuel cell water vapor inlet 111. The cut-off edges 121b form the channel 3b for receiving the oxygen outlet 113, and the cut-off edges 121c form the channel 3c for receiving the methanation unit 200. Of course, a further cut-off edge may provide an additional channel for receiving a residual gas duct.

Figure 12:
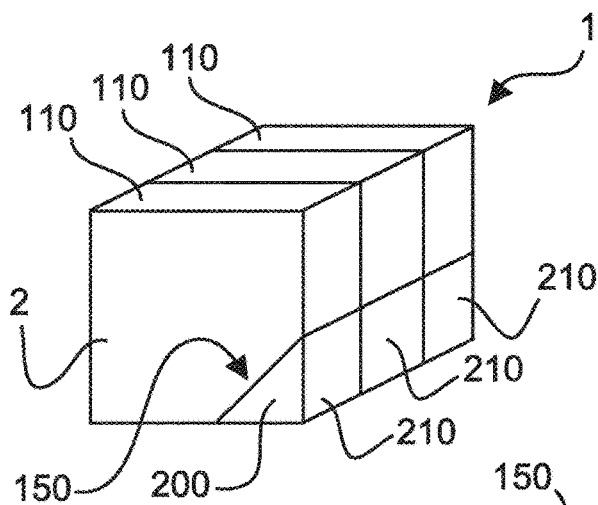
FIG. 12 illustrates the general structure of stacked fuel cell units having allocated methanation sub-sections.

FIG. 12 illustrates a structure of a fuel cell arrangement 1, within a housing 2, wherein each fuel cell unit 110 is allocated to a corresponding subsection 210 of the methanation unit 200. However, it should be noted that the fuel cell arrangement may also work if there is no one-to-one correspondence from a methanation sub-section 210 and a respective fuel cell unit 110. The fuel cell units 110 can also be allocated to a common methanation unit 200. The plurality of fuel cell units 110 can be arranged as a stack of fuel cell units 110. Each of the fuel cell units 110 can be arranged adjacent to the methanation unit 200. Each of the plurality of fuel cell units 110 can share a common wall with the methanation unit. The methanation unit 200 can be designed as a stack of catalyst sub section 210. Each of the catalyst sub sections 210 can be designed like a methanation unit 200 as described before with respect to any of FIGS. 2 to 10 and FIG. 13. Thus, the entire methanation unit 200 can have a plurality of: methanation unit hydrogen inlets 212, methanation unit hydrogen inlets 213, methanation unit carbon oxide inlets 214, carbon oxide inlet valves 215, methanation unit methane outlets 216, methanation unit heating units/elements 217, methanation unit sensors 218, catalyst pressure control valves 219, methanation unit residual hydrogen gas outlets 220, methanation unit residual carbon oxide gas outlets 221, methanation unit active wall surface sections or catalysts 222, methanation unit hydrogen residual gas controlling valves 232, methanation unit methane controlling valves 233, hydrogen residual gas pumping units/pressure gradient generators 242, methane pumping units/pressure gradient generators 243, pressure control pumping units/pressure gradient generators 244, carbon oxide feeding pumping units/pressure gradient generators, 245 and carbon oxide residual gas pumping units/pressure gradient generators 246. It should be noted that some of the before mentioned valves, inlets, outlets, pumps or generators may be provided once for the methanation unit 200 or a plural times.

In the arrangement of FIGS. 10 to 12, the hydrogen outlet 112 of each of the plurality of fuel cell units 110 is coupled to at least one of the hydrogen inlets 212 of the methanation unit 200.

Figure 13:
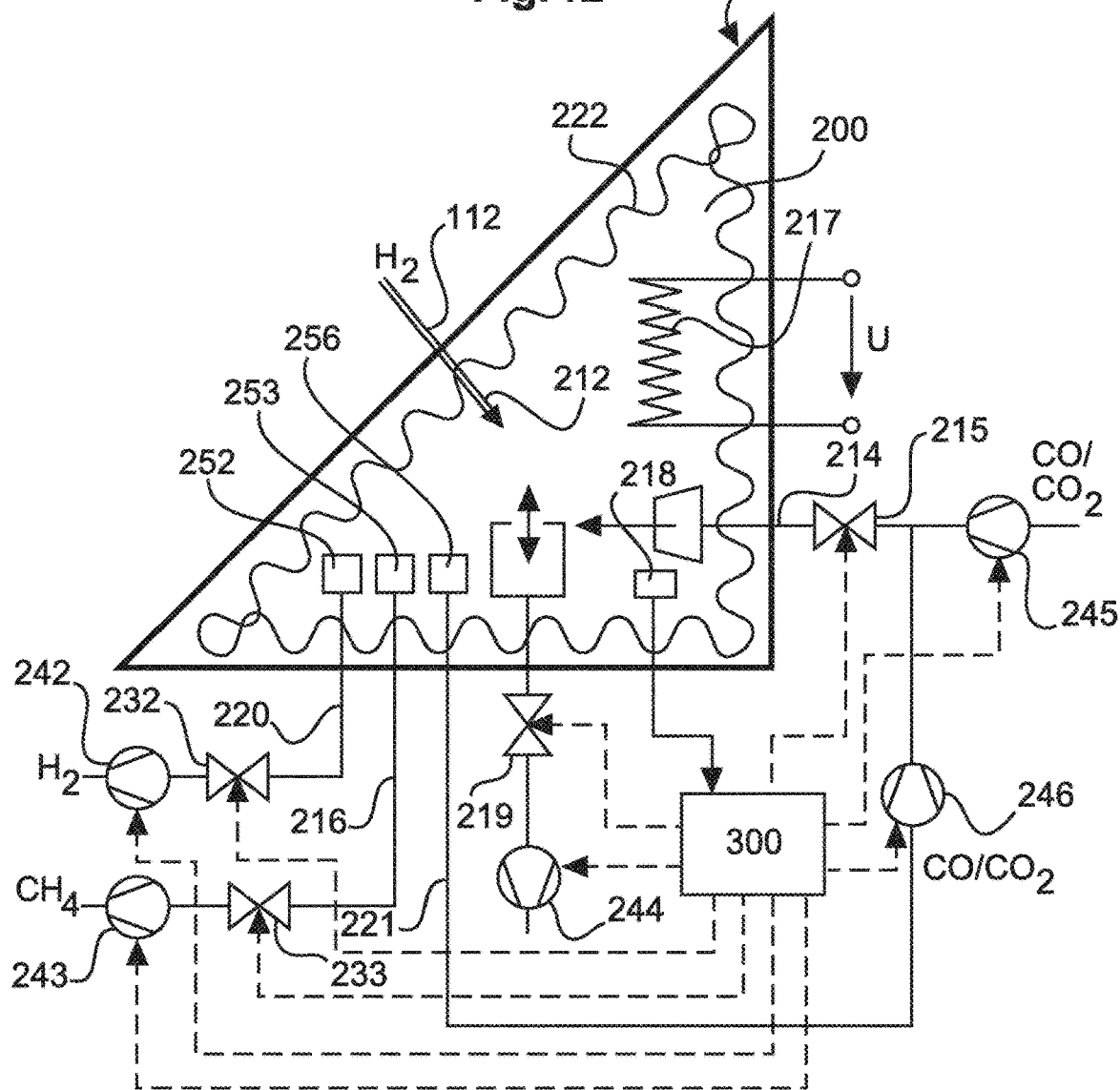
FIG. 13 illustrates a schematic overview of the respective inputs and outputs of the methanation unit including the valves, the controlling paths, and secondary elements, like pumps and ducts.

Further, FIG. 13 illustrates in further detail the elements of the methanation unit. Again, elements with same functions are denoted with same reference numerals, as described above, and will not be described in further detail. In addition to the hydrogen input 212, and the heating section 217, the inlets and the outlets may be provided with controlling valves, and for example devices for providing a flow or increasing the pressure, like pumps. In particular, the carbon oxide inlet 214 may be provided with a carbon oxide controlling valve 215, and the carbon oxide may be increased in pressure by a carbon oxide pump 245. Also the residual carbon oxide from the residual carbon oxide outlet 221 may be fed back by a carbon oxide pump 246. It should be noted that in addition or instead of one or both pumps 245 and 246, a common pump may be provided directly before or behind the carbon oxide controlling valve 215. The carbon oxide residual output 221 may be provided with carbon oxide filter 256, so as to ensure that only carbon oxide leaves the methanation unit 200 in a planned manner. In the same way, the residual hydrogen outlet 220 may be provided with the hydrogen filter 252 to ensure that only hydrogen leaves the methanation unit through the hydrogen outlet 220. The hydrogen controlling valve 232 may be used for controlling the amount of hydrogen. The outlet may be supported by a hydrogen pump 242. Also the methane outlet 216 may be provided with a methane filter 253, and the outlet amount of methane may be controlled by the methane controlling valve 233. The outlet of the methane may be supported by a methane pump 243. Also the pressure valve 219 may be in line with a pressure pump 244 to provide the respective pressure gradient. It should be noted that also a sensing device 218 may be provided, which may sense the operation condition within the methanation unit 200. The sensing element 218 may, for example, sense the concentration of hydrogen, the concentration of methane, the concentration of carbon oxide, etc. The sensing unit may also detect the pressure condition within the methanation unit, as well as the temperature. It should be noted that the sensing element 218 may comprise a plurality of separate sensors, which sensors may be distributed over the extension of the methanation unit. It should be understood that depending on the requirements, several kinds of sensors, like temperature sensors, pressure sensors, carbon oxide concentration sensors, hydrogen concentration sensors, and methane concentration sensors may be distributed along the extension of the methanation unit, so as to get a full impression on the operation conditions with respect to several operation parameters of the methanation unit. The control of the several valves, for example valve 215, 219, 232, 233 may be controlled by the controlling unit 300. Also the pumps 242, 243, 244, 245, 246 may be controlled by the controlling unit 300.

The control unit may control the inlet valve 215 so as to control the inlet of carbon oxide, e.g. carbon monoxide and/or carbon dioxide, based on a determined concentration of e.g. carbon monoxide and/or carbon dioxide and/or methane in the outlet and/or the methanation unit. Sensors 218 can be provided for determining the above mentioned concentration. Controlling may be conducted motor driven. The controlling process may e.g. control the process so as to achieve a maximum conversation rate of carbon oxide to methane. As methanation is a catalytic process, which process requires activation energy, the optimum concentration of carbon oxide, e.g. carbon monoxide and/or carbon dioxide may vary depending on the pressure and temperature. The control unit 300 may have included a look-up table, either in numeric form or in algorithmic form. The look-up table may have included relations between at least one of temperature, pressure, concentration of carbon monoxide, concentration of carbon dioxide on the one hand and a sensor signal on the other hand. In case the concentration of carbon oxide is too low, the control unit may activate the inlet valve 215 so that additional carbon oxide is fed. In case the concentration is too high, the control unit 300 may activate the outlet valve 219 so that gas is released.

Figure 14:
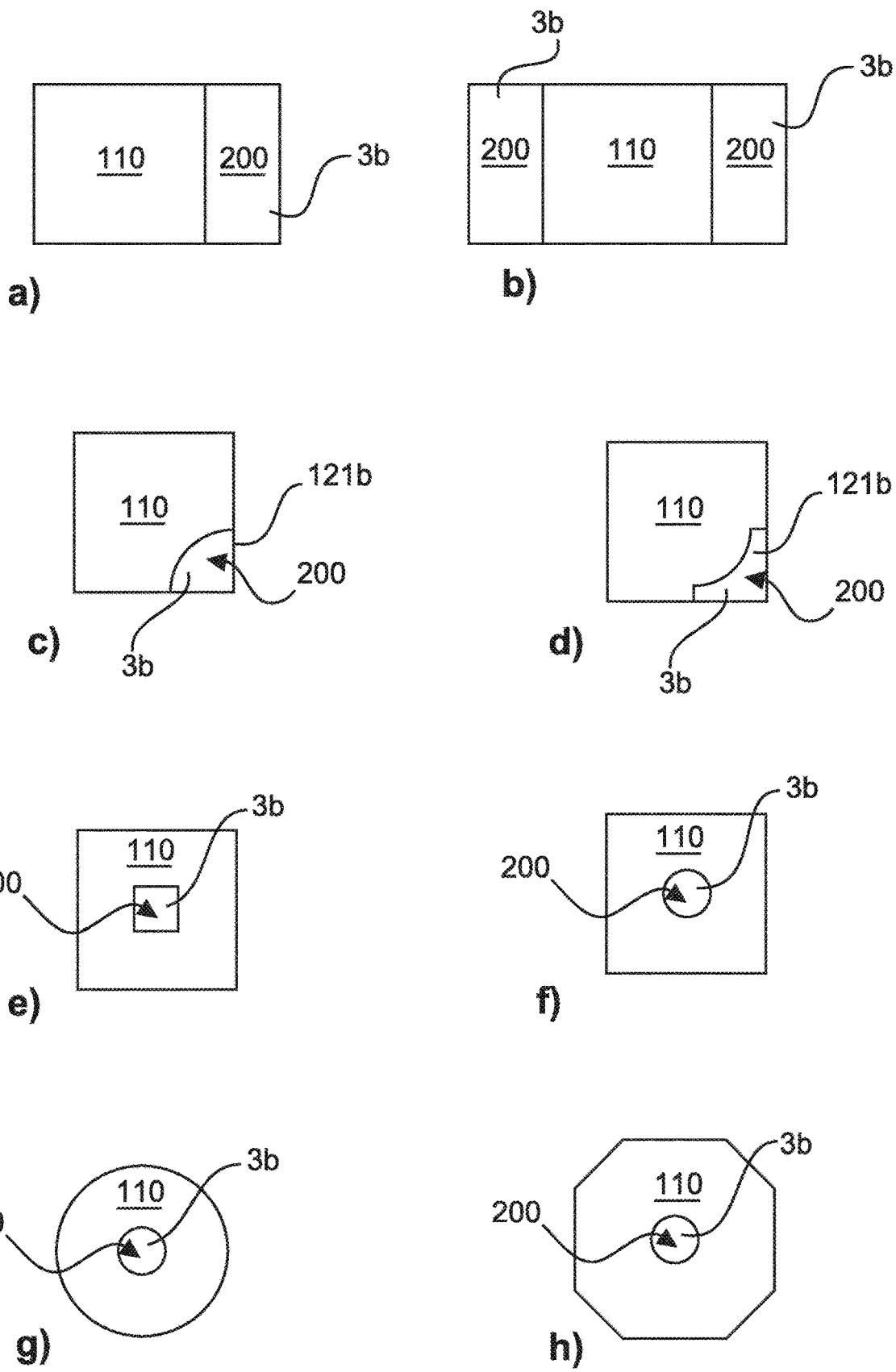
FIG. 14 $a$ to $h$ illustrate a variety of geometries of a methanation unit 200 beside a fuel cell unit 110.

FIG. 14 illustrates a variety of geometries of a methanation unit 200 beside a fuel cell unit 110. It should be understood that each of the varieties of FIG. 14 may also be implemented by a plurality of fuel cell units 110, being arranged in a stacked manner, wherein each of the fuel cell units 110 share a common wall section with the methanation unit 200. In FIG. 14 only one fuel cell unit is illustrated, namely the first fuel cell unit, which first fuel cell units hides the further fuel cell units in FIG. 14. FIG. 14a illustrates an embodiment having arranged the methanation unit 200 beside one side of the fuel cell unit(s) 110. FIG. 14b illustrates an embodiment having arranged two methanation units 200 beside two different wall sections of the fuel cell unit(s) 110. FIG. 14c illustrates an embodiment having arranged the methanation unit 200 at a cut off corner or cut of edge of the fuel cell unit(s) 110. The common wall between the fuel cell unit 110 and the methanation unit 200 is convex seen from the fuel cell side. FIG. 14d illustrates an embodiment similar to that of FIG. 14c, but having a concave common wall seen from the fuel cell side. FIG. 14e illustrates an embodiment having a methanation unit embedded in the fuel cell unit(s). The methanation unit 200 forms a channel through the fuel cell units 110. Outer cross sectional shape of the fuel cell unit and the methanation unit are rectangular, or squared. FIG. 14f illustrates a similar embodiment, but having an elliptical, oval or circular cross section of the embedded methanation unit 200. FIG. 14g illustrates an embodiment having an elliptical, oval or circular cross section of the fuel cell unit 110 having embedded the methanation unit, which can be circular, oval or rectangular or polygonal. FIG. 14h illustrates an embodiment having a polygonal cross section of the fuel cell unit(s) 110. The polygonal cross section may be octagonal or hexagonal.

An octagonal cross section allows a tight packing having spaces there between for feeding conduits. A hexagonal cross section allows a tight packing like a honey comb when having embedded the feeding conduits in the fuel cell unit(s), which is not illustrated in detail in FIG. 14h.

It should be noted that the particular controlling of the feedback of gas, in particular the feedback of carbon oxide, i.e. carbon monoxide and/or carbon dioxide, the feedback of hydrogen, the controlling of the temperature, etc. may increase the efficiency of the methanation process, so that the entire efficiency of a fuel cell arrangement may be significantly increased.

It should be noted that the term "comprising" does not exclude other elements or steps, and that "a" or "an" does not exclude a plurality. Also elements described in association with the different embodiments may be combined.

It should be noted that the reference signs in the claims shall not be construed as limiting the scope of the claims.

REFERENCE LIST 1 fuel cell arrangement
2 housing of fuel cell arrangement
3, 3a, 3b, 3c channel for ducting a gas
110 fuel cell unit
111 fuel cell water (vapor) inlet
112 fuel cell hydrogen outlet
113 fuel cell oxygen outlet
114 fuel cell cathode
115 fuel cell membrane
116 fuel cell membrane controlling electrode
117 membrane controlling electrode controlling unit
118 fuel cell anode
119 di/dt measuring unit
120 distribution plates
121, 121a/b/c fuel cell unit cut-off edges
150 common wall between methanation unit and fuel cell unit
200 methanation unit
210 methanation sub-section
212 methanation unit hydrogen inlet
213 methanation unit hydrogen inlet
214 methanation unit carbon oxide inlet
215 carbon oxide inlet valve
216 methanation unit methane outlet
217 methanation unit heating unit/element
218 methanation unit sensor
219 methanation unit pressure control valve
220 methanation unit residual hydrogen gas outlet
221 methanation unit residual carbon oxide gas outlet
222 methanation unit active wall surface section, catalyst
232 methanation unit hydrogen residual gas controlling valve
233 methanation unit methane controlling valve
242 hydrogen residual gas pumping unit/pressure gradient generator
243 methane pumping unit/pressure gradient generator
244 pressure control pumping unit/pressure gradient generator
245 carbon oxide feeding pumping unit/pressure gradient generator
246 carbon oxide residual gas pumping unit/pressure gradient generator
300 controlling unit

The invention claimed is:

1. Fuel cell arrangement comprising
a first fuel cell unit,
a methanation unit and
a control unit,
wherein the first fuel cell unit comprises
   an active part for converting water into hydrogen and oxygen,
   a water inlet,
   a hydrogen outlet,
   an oxygen outlet,
wherein the methanation unit comprises
   a catalyst,
   a hydrogen inlet,
   a carbon oxide inlet having a first controllable valve,
   a methane outlet,
wherein the hydrogen outlet of the first fuel cell unit is coupled to the hydrogen inlet of the methanation unit,
wherein the methanation unit is adapted to convert by the catalyst hydrogen and carbon oxide into methane,
wherein the methanation unit is arranged beside the first fuel cell unit in a manner to allow a heat transfer from the methanation unit to the first fuel cell unit,
wherein the control unit is adapted to control the first controllable valve so as to obtain an optimum converting process to convert hydrogen and carbon oxide into methane,
wherein the methanation unit and the first fuel cell unit share a common wall, wherein the common wall allows a heat transfer between the methanation unit and the first fuel cell unit, and
wherein the common wall has openings or a porous area for transferring hydrogen from a fuel cell cavity to a catalyst cavity that are separated by the common wall.

2. Fuel cell arrangement according to claim 1, comprising a plurality of fuel cell units, one thereof is the first fuel cell unit, wherein each of the plurality of fuel cell units comprises
an active part for converting water into hydrogen and oxygen,
a water inlet,
a hydrogen outlet,
an oxygen outlet,
wherein the methanation unit is arranged beside each of the plurality of fuel cell units in a manner to allow a heat transfer from the methanation unit to each of the plurality of fuel cell units,
wherein the methanation unit further comprises a plurality of a carbon oxide inlets each having a controllable valve,
wherein the hydrogen outlet of each of the plurality of fuel cell units is coupled to the hydrogen inlet of the methanation unit,
wherein the control unit is adapted to control the plurality of controllable valves so as to obtain an optimum converting process to convert hydrogen and carbon oxide into methane,
wherein each of the plurality of fuel cell units shares a common wall with the methanation unit, wherein the common wall allows a heat transfer between the methanation unit and each of the plurality of fuel cell units.

3. Fuel cell arrangement according to claim 2, wherein the methanation unit comprises a plurality of methanation sub-sections, wherein each of the methanation sub-sections is allocated to at least one of a plurality of fuel cell units, wherein each of the methanation sub-sections comprises one of a plurality of carbon oxide inlets each having a controllable valve.

4. Fuel cell arrangement according to claim 1, wherein the methanation unit comprises at least one sensor for sensing operation parameters in the methanation unit, the sensor is selected from a group, the group consisting of pressure sensor, methane sensor, hydrogen sensor, temperature sensor, carbon oxide sensor, wherein the control unit is adapted to control the first controllable valve based on a determined carbon oxide concentration.

5. Fuel cell arrangement according to claim 2, wherein the control unit is adapted to control each of the plurality of controllable valves separately based on a determined carbon oxide concentration.

6. Fuel cell arrangement according to claim 1, wherein the methanation unit comprises at least one pressure controlling valve, wherein the pressure controlling valve is controllable upon sensed operation parameters in the methanation unit.

7. Fuel cell arrangement according to claim 1, wherein the methanation unit further comprises at least one hydrogen residual gas outlet.

8. Fuel cell arrangement according to claim 1, wherein the methanation unit further comprises at least one carbon oxide residual gas outlet.

9. Fuel cell arrangement according to claim 2, wherein each of the plurality of fuel cell units comprises a cathode and an anode, and a fuel cell membrane between the cathode and the anode, wherein at least one fuel cell membrane comprises a control electrode arrangement and the fuel cell arrangement further comprises an electrode arrangement controlling unit.

10. Fuel cell arrangement according to claim 9, wherein the fuel cell arrangement comprises at least one di/dt measuring unit, wherein the electrode arrangement controlling unit is adapted to control the electrode arrangement based on measured di/dt.

11. Fuel cell arrangement according to claim 1, wherein the methanation unit comprises an active wall surface section being coated with a catalyst agent, wherein the catalyst agent is a solid phase catalysts material selected from a group, the group consisting of: nickel, aluminum oxide, zirconium oxide, noble metals, in particular platinum and platinum alloys.

12. Fuel cell arrangement according to claim 2, further comprising a housing having a rectangular cross section, wherein the plurality of fuel cell units are stacked, wherein each of the fuel cell units has a rectangular envelope with at least one cut-off edge, wherein the at least one cut-off edge of each of the fuel cell units correspond to each other so that a space between a rectangular housing and the corresponding at least one cut-off edge forms a channel for ducting a gas.

13. Fuel cell arrangement according to claim 2, further comprising a rectangular housing, wherein each fuel cell unit has a rectangular envelope with three cut-off edges, wherein the three cut-off edges of each fuel cell unit correspond to each other so that a space between the rectangular housing and the corresponding cut-off edges form at least three channels for ducting gas, a first channel serving for providing water vapor, a second channel serving for oxygen collection and a third channel serving for receiving the methanation unit, wherein the hydrogen outlet of each of the plurality of fuel cell units is coupled to at least one of the hydrogen inlets of the methanation unit.

14. Fuel cell arrangement according to claim 2, wherein the common wall between the methanation unit and each of the plurality of fuel cell units comprises the common wall between the methanation unit and the first fuel cell unit.

* * * * *